United States Patent
Park (10) Patent No.: US 8,603,166 B2
(45) Date of Patent: *Dec. 10, 2013

(54) INTRAOCULAR LENS ASSEMBLY

(76) Inventor: Kyong Jin Park, Gangnam-gu (KR)

( * ) Notice: Subject to any disclaimer, the term of this patent is extended or adjusted under 35 U.S.C. 154(b) by 962 days.

This patent is subject to a terminal disclaimer.

(21) Appl. No.: 12/530,249

(22) PCT Filed: Sep. 21, 2007

(86) PCT No.: PCT/KR2007/004633
§ 371 (c)(1), (2), (4) Date: Sep. 8, 2009

(87) PCT Pub. No.: WO2008/108525
PCT Pub. Date: Sep. 12, 2008

(65) Prior Publication Data
US 2010/0016963 A1    Jan. 21, 2010

(30) Foreign Application Priority Data

Mar. 8, 2007 (KR) .................. 10-2007-0022872

(51) Int. Cl.
*A61F 2/16* (2006.01)

(52) U.S. Cl.
USPC ......... 623/6.23; 623/6.32; 623/6.39; 623/6.4; 623/6.41; 623/6.34; 623/6.42; 623/6.43; 623/6.49

(58) Field of Classification Search
USPC ...................... 623/6.13, 6.49–6.55
See application file for complete search history.

(56) References Cited

U.S. PATENT DOCUMENTS

| | | | |
|---|---|---|---|
| 4,451,938 A | 6/1984 | Kelman | |
| 5,152,789 A | 10/1992 | Willis | |
| 6,013,101 A * | 1/2000 | Israel | 623/6.43 |
| 6,051,024 A | 4/2000 | Cummings | |
| 6,749,634 B2 * | 6/2004 | Hanna | 623/6.37 |
| 7,048,760 B2 | 5/2006 | Cummings | |
| 7,097,660 B2 | 8/2006 | Portney | |
| 7,261,737 B2 * | 8/2007 | Esch et al. | 623/6.37 |
| 2003/0130732 A1 * | 7/2003 | Sarfarazi | 623/6.13 |
| 2003/0135272 A1 | 7/2003 | Brady et al. | |
| 2003/0149479 A1 | 8/2003 | Snyder et al. | |
| 2003/0204254 A1 | 10/2003 | Peng et al. | |
| 2004/0082994 A1 | 4/2004 | Woods et al. | |
| 2004/0082995 A1 * | 4/2004 | Woods | 623/6.34 |
| 2004/0169816 A1 | 9/2004 | Esch | |
| 2006/0001186 A1 | 1/2006 | Richardson et al. | |
| 2006/0244904 A1 | 11/2006 | Hong et al. | |

FOREIGN PATENT DOCUMENTS

FR    2784575    *  2/2000
WO    00071245 A1    11/2000

OTHER PUBLICATIONS

International Search Report dated Jan. 3, 2008 issued in corresponding PCT Application No. PCT/KR2007/004633, 2 pages.

* cited by examiner

*Primary Examiner* — David H Willse
*Assistant Examiner* — Tiffany Shipmon
(74) *Attorney, Agent, or Firm* — Edwards Wildman Palmer LLP (57) ABSTRACT

Disclosed is an intraocular lens assembly provided inside a capsular sac. The intraocular lens assembly according to one embodiment of the present invention includes an intraocular lens and an intraocular lens supporter, and therefore the intraocular lens assembly may be useful to transfer a force to the intraocular lens, inserted inwardly into the capsular sac, to allow the intraocular lens to move like a natural eye lens, the force being generated from the ciliaris muscle and transferred through the zonule of Zinn and the capsular sac.

36 Claims, 8 Drawing Sheets

Fig. 23

INTRAOCULAR LENS ASSEMBLY

TECHNICAL FIELD

The present invention relates to an intraocular lens assembly, and more particularly to an intraocular lens assembly provided inside a capsular sac.

BACKGROUND ART

In recent years, as one of treatment methods of ophthalmic diseases that are abnormal in eye lens such as cataract, a method has been increasingly used throughout the world, comprising steps of removing eye lens contents from a capsular sac and inserting an artificially produced intraocular lens into their space.

In the case of the insertion of the intraocular lens, the intraocular lens may give an opaque sight to patients instead of their own natural eye lens. However, regardless of its many advantages, the intraocular lens has problems that a capsular sac into which the intraocular lens is inserted is contracted after the insertion of the intraocular lens.

Accordingly, a new method has been increasingly used, comprising steps of inserting a capsular tension ring into an equatorial region of a capsular sac prior to the insertion of the intraocular lens and fixing the intraocular lens in the capsular tension ring.

A capsular tension ring, which is referred to as open or closed ring formations, is effective in partially relieving contraction of a capsular sac, partially maintaining a shape of the capsular sac from which an eye lens is removed, and easily supporting the inserted intraocular lens.

In order to use a capsular tension ring in a more effective manner, there have been recently ardent studies to develop a structure for easily inserting a capsular tension ring, a structure for preventing a posterior capsular opacity, etc.

However, a more serious problem in the conventional surgical operation of insertion of an intraocular lens is that an anterior capsule and a posterior capsule of a capsular sac are adhere to each other after the surgical operation, which leads to the loss of its inherent function to control a thickness of an eye lens by relaxing and contracting zonule of Zinn.

That is to say, the problems is that a patient does not ensure a sight through active three-dimensional movements of an intraocular lens along objects to be of, but ensures a passive sight according to the predetermined power of an intraocular lens.

Hereinafter, the conventional surgical operation of insertion of an intraocular lens will be described in detail with reference to the accompanying drawings.

Figure 1:
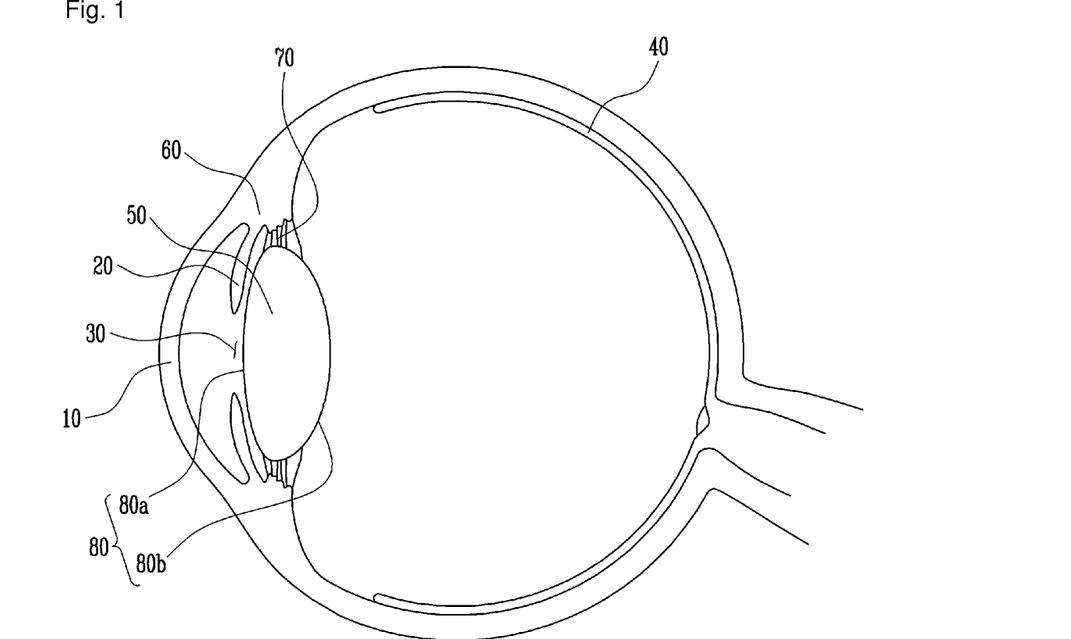
FIG. 1 is a cross-sectional view showing a human eyeball.
Figure 2:
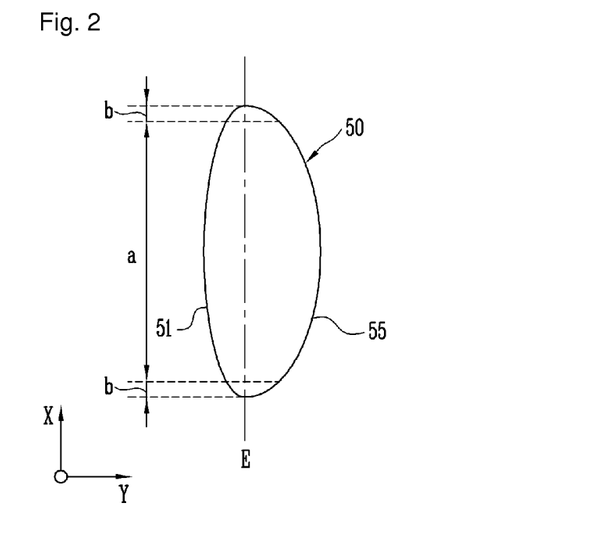
FIG. 2 is a cross-sectional view showing a structure of a natural eye lens.

FIG. 1 is a cross-sectional view showing a human eyeball, and FIG. 2 is a cross-sectional view showing a structure of a natural eye lens. Referring to FIGS. 1 and 2, a cornea 10 is a transparent avascular tissue disposed in the outermost region of the eye and protects an eyeball. Also, the cornea serves to reflect the light together with the eye lens. An iris 20 functions as the iris of a camera by adjusting the intensity of the light entering the eye. Also, a pupil 30 is a hole in the center of the iris 20, and adjusts the intensity of the light entering the retina 40 by contracting the hole under the bright light and expanding the hole under the dark light.

An eye lens 50 is a colorless and transparent avascular structure having a convex lens shape in both sides, and arranged in the back of the iris 20. The eye lens 50 is an organ that takes part in reflecting the light entering the eye together with the cornea 10, and its shape is changed according to the contraction and relaxation of a ciliaris muscle 60 and a zonule of Zinn 70 coupled to the ciliaris muscle 60.

Presbyopia is a state that the hardness of the eye lens 50 increases with the age, and therefore the shape of the eye lens 50 is not changed even if the ciliaris muscle 60 contracts, and the cataract is a disease that the eye lens 50 becomes opaque with the age.

The eye lens 50 is filled inside a capsular sac 80, and the capsular sac 80 is composed of an anterior capsule 80a and a posterior capsule 80b, each of which is in contact with an anterior surface 51 and a posterior surface 55 of the eye lens 50. At this time, the anterior surface 51 and the posterior surface 55 of the eye lens 50 are coupled to each other in an equator (E). Each of the anterior surface 51 and the posterior surface 55 is divided into a central region (a) and an equatorial region (b) according to the distance from the equator (E). The central region (a) of the anterior surface 51 has a smaller curvature than the central region (a) of the posterior surface 55, and the equatorial region (b) of the anterior surface 51 has a larger curvature than the equatorial region (b) of the posterior surface 55.

The zonule of Zinn 70 is coupled along an edge of the capsular sac 80. The zonule of Zinn 70 is a kind of a fibrous tissue that couples the capsular sac 80 to the ciliaris muscle 60, and composed of a first zonule portion coupled to the center of the equatorial region in which the anterior capsule 80a and the posterior capsule 80b of the capsular sac 80 meets; and a second zonule portion coupled to a circumference of the equatorial region.

Figure 3:
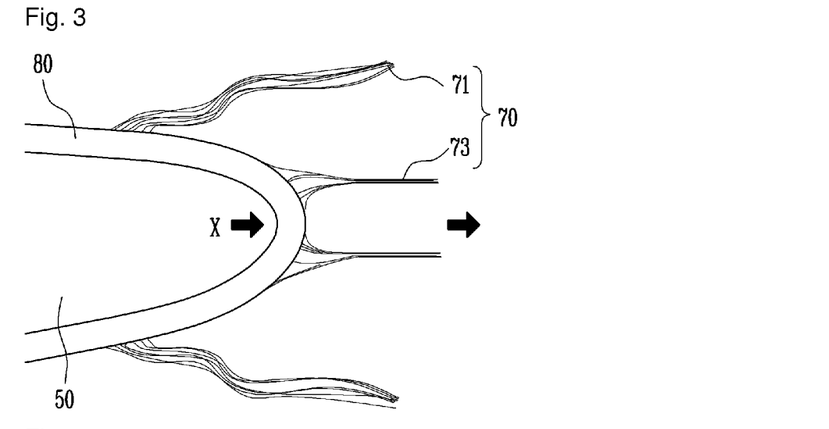
FIG. 3 and FIG. 4 are illustrative views showing interactions a zonule of Zinn and an eye lens when focused on a long distance and a short distance object, respectively.
Figure 4:
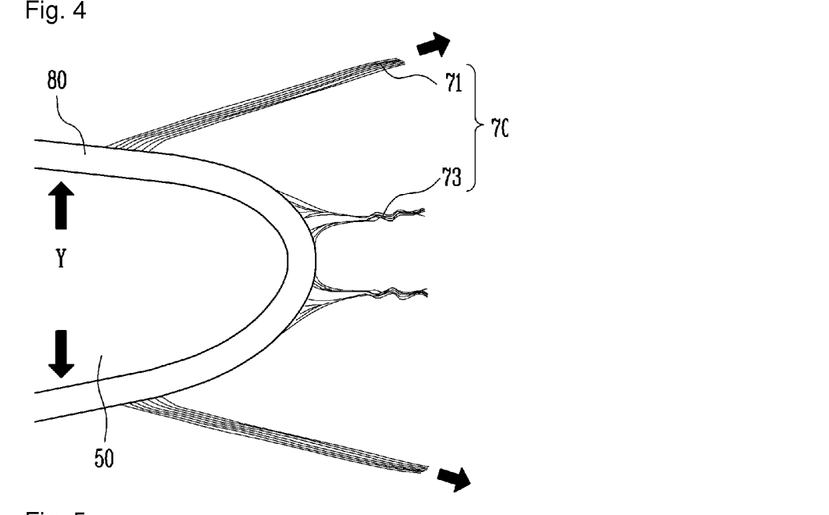

FIG. 3 and FIG. 4 are illustrative views showing an interaction of a zonule of Zinn, an eye lens and a capsular sac when focus on a long distance object and a short distance object, respectively. In this application, a Y direction represents a visual axis direction of an eye lens, and an X direction represents an equatorial direction of an eye lens. The visual axis direction of the eye lens means a direction that the light enters an eye lens 50 through a pupil, and the equatorial direction means a direction that, as a vertical direction of the visual axis direction, connects a point that an anterior capsule and a posterior capsule of an eye lens meets.

In the zonule of Zinn 70, a first zonule portion 73 coupled to the center of the equatorial region of the capsular sac 80 is pulled taut and a second zonule portion 71 coupled to the circumference of the equatorial region of the capsular sac 80 is relaxed when focus on a long distance object. As a result, the capsular sac 80 is extended in an X direction of the eye lens 50, and therefore the eye lens 50 arranged inside the capsular sac 80 is extended in the same direction (X).

In the zonule of Zinn 70, the first zonule portion 73 coupled to the center of the equatorial region of the capsular sac 80 is relaxed and the second zonule portion 71 coupled to the circumference of the equatorial region of the capsular sac 80 is pulled taut when focused on a short distance object. As a result, the capsular sac 80 is projected in a Y direction of the eye lens 50, and therefore the eye lens 50 arranged inside the capsular sac 80 is extended in the same direction. Here, the Y direction of the eye lens 50 is a direction where the light is incident on the eye lens 50 through the pupil, and the X direction is a direction that is vertical to the Y direction.

As described above, the capsular sac 80 having a natural eye lens disposed therein is coupled to the zonule of Zinn 70, and therefore takes part in actively deforming shapes of the natural eye lens, but the use of the conventional intraocular lens and capsular tension ring forces the capsular sac to contract, which leads to the substantial loss of its functions.

In particular, a ciliaris muscle, which is coupled to a zonule of Zinn to take part in the shape deformation of an eye lens, is a visceral muscle that maintains the endless function to the death. Therefore, the conventional method of artificially removing an ability of healthy ciliaris muscle must be improved in that an ability of ciliaris muscle is not damaged although the eye lens is damaged.

Meanwhile, the conventional intraocular lens and capsular tension ring are disclosed in various literatures including U.S. Patent Publication Nos. 2006/0244904, 2006/0001186 and 2003/0149479.

DISCLOSURE OF INVENTION

Technical Problem

Accordingly, the present invention is designed to solve such drawbacks of the prior art, and therefore an object of the present invention is to provide an intraocular lens assembly that is configured so that an intraocular lens can have a shape deformation that is similar to operations of a natural eye lens.

Technical Solution

One embodiment of the present invention is achieved by providing an intraocular lens assembly inserted inwardly into a capsular sac including: an intraocular lens including an optic portion including a first optic body whose central region has a smaller thickness than a circumference of the central region and a second optic body coupled to the first optic body and whose central region has the same or higher thickness as/than the first optic body, and a haptic portion including a connection bar coupled to the optic portion and first support bar coupled to a circumference of the connection bar to be in contact with an inner surface of the capsular sac; and an intraocular lens supporter that is inserted into a capsular sac including a first face coming in contact with an inner surface of the capsular sac in at least one point as a structural body that is extended along an equatorial region of the capsular sac, and a second face arranged opposite to the first face, wherein, the intraocular lens is a structural body that is extended along an equatorial region of the capsular sac and in a section where the structural body is cut along a virtual plane in a visual axis direction (Y direction) of an eye lens, the first face is provided at a length as much as ¾ to 3 times of a length (d5) of a region where a zonule of Zinn is coupled to an outer surface of the capsular sac.

At this time, the first optic body is preferably made of materials that are more flexible than the second optic body.

Also, the first optic body preferably includes an inner surface and an outer surface, the inner surface and the outer surface is preferably a spherical surface or an aspheric surface, and the inner surface is preferably a spherical surface having a higher curvature than the outer surface, or a more aspheric surface.

Also, the first support bar preferably has a surface that is in contact with an inner surface of the capsular sac and has a round shape.

Also, the connection bar may be a shaft bar-shaped structural body coupled to at least two sections in a circumference of the optic portion.

Also, the first support bar may be a structural body for coupling at least two ends of the shaft bars of the connection bar.

Also, the first support may be a ring-shaped structural body for coupling all ends of the shaft bars of the connection bar.

Also, the first support bar of the haptic portion may be made of flexible materials that are more flexible than the shaft bar, and the optic portion may be made of flexible materials that are more flexible than the first support bar.

Also, both ends of the shaft bar preferably have a larger cross-sectional area than a central region of the shaft bar.

Also, the both ends of the optic portion of the shaft bar preferably further include a ring-shaped second support bar for coupling ends of the optic portion.

Also, an inner surface of the second support bar preferably has a concave shape toward the central region of the optic portion.

Also, the second support bar may be formed in a circumference of the optic portion.

Also, the second support bar may be includes inside the optic portion.

Also, the connection bar may be a disk-shaped structural body coupled to the entire section of the circumference of the optic portion.

Also, the connection bar may be a disk-shaped structural body coupled to at least two sections of the circumference of the optic portion and divided into at least two sections.

Also, the first support bar is preferably formed around an end of the disk-shaped connection bar.

Also, the optic portion and the first support bar are preferably made of flexible materials that more flexible than the connection bar.

Also, the optic portion and the first support bar are preferably made of the same flexible materials as the connection bar, and formed in a thinner thickness than the connection bar.

Also, the first support bar is preferably a structural body that is extended along an end of the connection bar, and a surface of the first support bar that is in contact with an inner surface of the intraocular lens supporter preferably accords with a shape of the inner surface of the intraocular lens supporter.

Also, a flowing space is preferably further provided inside the intraocular lens.

Also, the flowing space is preferably provided at least between the first optic body and the second optic body.

Also, the flowing space may include a first space portion provided between the first optic body and the second optic body; a second space portion provided inside the connection bar; and a third space portion provided inside the first support bar.

Also, the first space portion, the second space portion and the third space portion are preferably coupled to each other.

Also, the flowing space is preferably filled with one selected from the group consisting of liquid, gas, and fluent solid.

Also, a shape of the first space portion is preferably formed in a convex lens shape having at least one convex surface.

Also, a shape of the first space portion is preferably formed in an aspheric convex lens shape having at least one aspheric surface.

Also, the second optic body preferably has a thinner thickness in its central region than its circumference.

Also, the second optic body preferably includes an inner surface and an outer surface, and the inner surface and the outer surface may be a spherical surface or an aspheric surface, and the inner surface is preferably a spherical surface or an aspheric surface having a larger curvature than the outer surface.

Also, the first optic body and the second optic body preferably have the same thickness, and preferably include sections that have an increasing thickness as their central regions approach their circumference, respectively.

Also, the liquid may be one selected from the group consisting of water, silicone, sodium hyaluronate, chondroitin sulfate, hydroxypropyl methylcellulose and polyacrylamide.

Also, the gas is preferably one selected from the group consisting of air, nitrogen, helium, neon and argon.

Also, materials of the intraocular lens and the intraocular lens supporter may be composed of one selected from the group consisting of silicone, silicone elastomer, silicone polymer, polydimethyl siloxane, polypropylene, polyimide, polybutester, polymethyl methacrylate (PMMA), Microplex PMMA, CQ-UV PMMA, acrylic resin, rigid acrylic, flexible acrylic, acrylic plastic, hydrophobic acrylic, hydrophilic acrylic, hydrophilic acrylic polymer, UV absorbing acrylate, methacrylate copolymer, butyl acrylate, polysiloxane elastomer, UV absorbing polysiloxane, collagen copolymer, gold, hydrogel, 2-hydroxyethyl methacrylate (HEMA), methyl methacrylate (MMA), cellulose acetate butylate (CAB), 2-hydroxy ethyl methacrylate (2-HAMA), n-vinyl pyrrolidone (NVP), polyvinyl pyrrolidone (PVP), methacrylic acid (MA), glycerol methacrylate (GMA), dimethyl siloxane (DMS), polyhydroxyethyl methacrylate (PHEMA), polyethyleneglycol methacrylate (PEGMMA), poly HEMA hydrogel, poly HEMA hydrogel with UV absorption, silicone hydrogel, GMA/HEMA, HEMA/PVP/MA, PVA, HEMA/PVA/MA, HEMA/PVA/MMA, HEMA/MMA, HEMA/NVP, HEMA/NVP/MA, HEMA/NVP/MMA, HEMA/Acryl, and HEMA/PC.

Also, a subsidiary supporter is preferably further provided between the intraocular lens and the intraocular lens supporter, the subsidiary supporter including a first face with a shape facing the second face of the intraocular lens supporter; and a second face with a shape facing the outer surface of the haptic portion of the intraocular lens.

Also, a surface facing the optic portion of the first support bar preferably includes a section that is formed at a thicker thickness than a surface facing the intraocular lens supporter.

Also, a surface facing the optic portion of the first support bar preferably includes a section that is formed of flexible materials that are less flexible than a surface facing the intraocular lens supporter.

Advantageous Effects

The intraocular lens assembly according to the present invention has an effect to transfer a force to the intraocular lens, inserted inwardly into the capsular sac, to allow the intraocular lens to operate like the natural eye lens, the force being generated from the ciliaris muscle and transferred through the zonule of Zinn and the capsular sac.

Accordingly, the intraocular lens assembly according to the present invention may be used for the intraocular lens operation in order to treat cataract, presbyopia, high myopia, etc. At the same time, the intraocular lens assembly according to the present invention may have a substitute effect on lasik operations or implantable contact lens (ICL) operations.

BRIEF DESCRIPTION OF THE DRAWINGS

These and/or other aspects and advantages of the invention will become apparent and more readily appreciated from the following description of the preferred embodiments, taken in conjunction with the accompanying drawings of which.

MODE FOR THE INVENTION

Hereinafter, preferable embodiments according to the present invention will be described with reference to the accompanying drawings.

Figure 5:
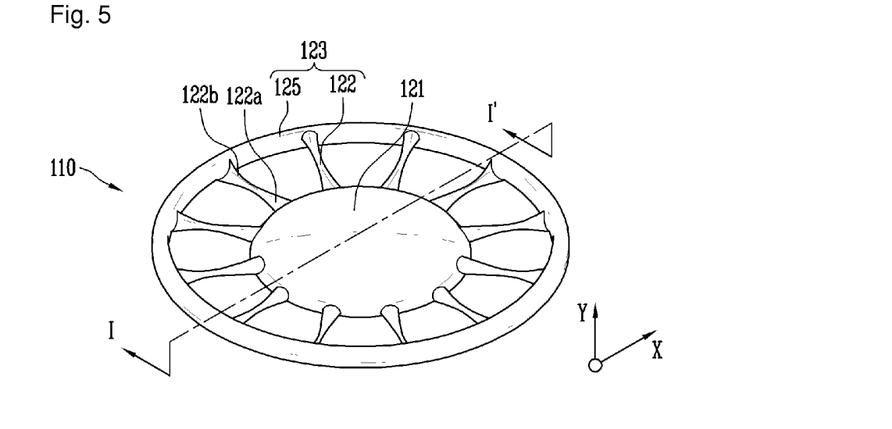
FIG. 5 is a perspective view showing an intraocular lens supporter according to the first embodiment of the present invention.
Figure 6:
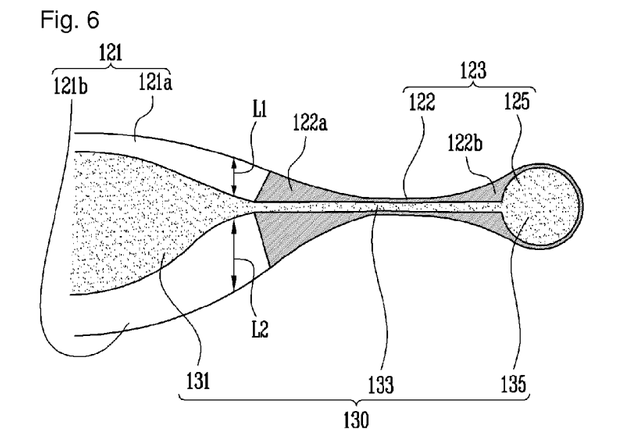
FIG. 6 is a cross-sectional view taken from a line I-I' as shown in FIG. 5.

FIG. 5 is a cross-sectional view showing an intraocular lens supporter according to one embodiment of the present invention, and FIG. 6 is a cross-sectional view taken from a line I-I' as shown in FIG. 5. Referring to FIGS. 5 and 6, the intraocular lens 110 is an artificial eye lens that is inserted inwardly into a capsular sac, and the intraocular lens 110 according to this embodiment is divided into an optic portion 121 and a haptic portion 123. The optic portion 121 is a portion that is arranged in the rear of a pupil in the eye and functions as a lens of a natural eye lens in an intraocular lens, and it has a convex lens shape.

The optic portion 121 includes a first optic body 121a that has an increasing thickness as its central region approaches its circumferential region, and a second optic body 121b coupled to the first optic body 121a, wherein a thickness of a central region of the second optic body 121b is thicker than the first optic body 121a. At this time, the first optic body 121a and the second optic body 121b may have different convexity as in the anterior surface and the posterior surface of a human eye lens. That is to say, a curvature of the first optic body 121a may be smaller than the second optic body 121b.

A thickness (L1) of the first optic body 121a is preferably smaller than a thickness (L2) of the second optic body 121b in the section cut along a virtual plane in a visual axis direction (Y direction) of the eye lens. This is for the purpose that the shape deformation of the first optic body 121a is more induced than the second optic body 121b. That is to say, if a fluid in a flowing space 130 as described later is gathered in the optic portion 121, the first optic body 121a of the optic portion 121 having a thinner thickness is more protruded to ensure similar movement to a human eye lens.

The first optic body 121a and the second optic body 121b are preferably configured so that they can be thinnest in their central regions, and grow thicker as their central regions approach their circumferences. (Inner surfaces of the first optic body and the second optic body become aspheric surfaces.) This is for the purpose of ensuring a better control ability, and therefore this is why the thinner a thickness of a central region of a membrane, the more a fluid moves toward the central region, which leads to a more convex center of the optic portion of the central region.

Meanwhile, shapes of the optic portion 121 are not limited thereto, but the optic portion 121 is preferably provided in a conventional convex lens shape. In this case, a diameter of the optic portion 121 may be provided in a diameter as much as 0.2 to 0.8 times of the total diameter of the intraocular lens 110.

To constitute an optic portion 121 composed of two pieces of a first optic body 121a and a second optic body 121b is for the purpose of facilitating a shape deformation of the optic portion 121.

The optic portion 121 is generally disposed in the center of the entire intraocular lens 110. However, the optic portion 121 may be manufactured so that its center can move by a predetermine distance, for example by 0.1 mm for patients having a very serious leaning inside an image on a pupil in the miosis.

Also, the intraocular lens has an astigmatic axis and may correct a patient astigmatism by according a mark of the intraocular lens to a mark of the inside of an image or an inside mark previously indicated in a patient cornea in the surgical operation.

The haptic portion 123 is coupled to the optic portion 121 from an edge of the optic portion 121, and includes at least two shaft bars 122 that are jointed with an inner surface of the capsular sac, or an inner surface of an intraocular lens supporter or a subsidiary supporter as described later, and supports optic portion 121 formed inside the capsular sac.

In this embodiment, the haptic portion 123 has a first support bar 125 for coupling ends 122b arranged opposite to the optic portions of at least two shaft bars 122 to a plurality of shaft bars 122. The shaft bars 122 of the haptic portion 123 are provided in at least two numbers to transfer a force to the intraocular lens 110 in balance.

Also, the first support bar 125 is provided to transfer a force, transferred from the intraocular lens supporter (a subsidiary supporter), to the intraocular lens 110 in more balance, and its outer surface preferably has a round shape as a ring-shaped structure to which the end 122b arranged opposite to the optic portion of the shaft bar 122 is coupled. At this time, a section of the first support bar 125 is smaller than the shaft bar 122.

Meanwhile, the optic portion 121 in the intraocular lens 110 is preferably made of flexible materials that are more flexible than the materials constituting the shaft bar 122 of the haptic portion, or in a thinner thickness. This is for the purpose of deforming a shape of the optic portion 121 effectively by a force transferred by the movement of the zonule of Zinn that is induced in the ciliaris muscle. Here, the term flexible means that a material is so soft to deform easily.

The shaft bar of the haptic portion 123 is made of a relatively more rigid material than the optic portion 121, or has suitable elasticity and restoring force for the mechanical deformation. In this case, it is possible to operate on an eye by cutting a relatively smaller eyeball.

At this time, the optic portion 121 and the haptic portion 123 are made of different materials, and therefore the intraocular lens 110 may be composed of a plurality of pieces. Also, the optic portion 121 and the haptic portion 123 may be composed of the same materials, but they may have different flexibility.

Also, the flexibility of the shaft bar 122 of the haptic portion 123 may be identical to, or different from the flexibility of the first support bar 125 of the haptic portion 123, and the shaft bar 122 and the first support bar 125 may be composed of at least two pieces, or composed of one piece. The first support bar 125 is a region that directly reflects a volume change in the intraocular lens supporter as described later according to the shape deformation of the zonule of Zinn, and therefore the shape deformation of the first support bar 125 is made more effectively if the flexible materials that are more flexible than the shaft bar 122 are used.

Meanwhile, both ends of the shaft bar preferably have a larger cross-sectional area than its central region. This is for the purpose that the shaft bar may be easily coupled to the optic portion 121 and the first support bar 125.

Meanwhile, a flowing space 130 filled with a fluid is provided inside the intraocular lens 110. The flowing space 130 is provided at least inside the optic portion 121 of the intraocular lens 110, and the flowing space 130 is filled with a fluid. In FIGS. 5 and 6, the flowing space 130 is composed of a first space portion 131 formed inside the optic portion 121; a second space portion 132 formed inside the shaft bar of the haptic portion 123; and a third space portion 135 formed in the first support bar 125 of the haptic portion 123. As a result, the fluid filled in the flowing space 130 moves through the first space portion 131, the second space portion 133 and the third space portion 135 of the flowing space 130 by means of external forces.

The fluid filled in the flowing space 130, as used herein, includes water, air, inert gas, silicone, viscoelastic materials. Examples of the inert gas include nitrogen, helium, neon, argon, etc. Examples of the viscoelastic materials, as used herein, may include sodium hyaluronate, chondroitin sulfate, hydroxypropyl methylcellulose, polyacrylamide, etc.

The optic portion 121 may function as a lens with a low power of glasses due to the low refractive index when the first space portion 131 is filled with gas or water, and therefore it is possible to manufacture a negative lens used for the extremely myopic operations.

The second space portion 133 is a space formed in the shaft bar 122. At this time, the shaft bar 122 functions as a kind of a connection tube to allow a fluid to flow between the first space portion 131 and the third space portion 135. In the case of patients that are diagnosed to be in an excessive flow of the fluid after the surgical operation, a material capable of controlling a flow of the fluid may be injected into the second space portion 133.

The third space portion 135 is a space formed in the first support bar 125 as described above, and the third space portion 135 is a portion that directly reflects a volume change of the intraocular lens supporter 210.

A material of the intraocular lens 110, that may be used herein, includes silicone, silicone elastomer, silicone polymer, polydimethyl siloxane, polypropylene, polyimide, polybutester, Polymethyl methacrylate (PMMA), Microplex PMMA, CQ-UV PMMA, acrylic resin, rigid acrylic, flexible acrylic, acrylic plastic, hydrophobic acrylic, hydrophilic acrylic, hydrophilic acrylic polymer, UV absorbing acrylate, methacrylate copolymer, butyl acrylate, polysiloxane elastomer, UV absorbing polysiloxane, collagen copolymer, gold, hydrogel, 2-hydroxyethyl methacrylate (HEMA), Methyl methacrylate (MMA), cellulose acetate butylate (CAB), 2-hydroxy ethyl methacrylate (2-HAMA), n-vinyl pyrrolidone (NVP), polyvinyl pyrrolidone (PVP), methacrylic acid (MA), Glycerol methacrylate (GMA), dimethyl siloxane (DMS), Polyhydroxyethyl methacrylate (PHEMA), polyethyleneglycol methacrylate (PEGMMA), poly HEMA hydrogel, poly HEMA hydrogel with UV absorption, silicone hydrogel, GMA/HEMA, HEMA/PVP/MA, PVA, HEMA/PVA/MA, HEMA/PVA/MMA, HEMA/MMA, HEMA/NVP, HEMA/NVP/MA, HEMA/NVP/MMA, HEMA/Acryl, and HEMA/PC.

Various modifications of the intraocular lens may be made in the present invention. That is to say, the intraocular lenses as shown in FIG. 7, FIG. 8, FIG. 9 and FIG. 10 may be used.

Figure 7:
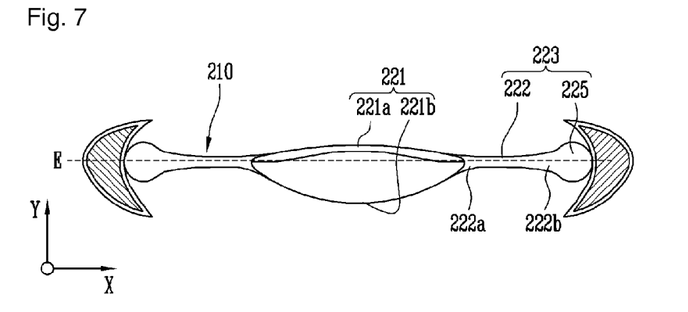
FIG. 7 to FIG. 10 are diagrams showing various modified examples of an intraocular lens used in the present invention.

FIG. 7 is a vertical cross-sectional view showing an intraocular lens having no flowing space and having support bars formed in each of ends of the shaft bar. At this time, the optic portion 221 includes a first optic body 221a having an increasing thickness as its central region approaches a circumferential region; and a second optic body 221b coupled to the first optic body 221a and having a larger thickness in its central region than the first optic body 221a. Meanwhile, shapes of the optic portion 221 are not limited thereto, but the optic portion 221 is preferably provided in a conventional convex lens shape. In this case, a diameter of the optic portion 221 may be provided in a diameter as much as 0.2 to 0.8 times of the total diameter of the intraocular lens 210.

To constitute an optic portion 221 composed of two pieces of a first optic body 221a and a second optic body 221b is for the purpose of facilitating a shape deformation of the optic portion 221.

The first optic body 221a has a smaller thickness than the second optic body 221b. This is for the purpose that the shape deformation of the first optic body 121a is more induced than the second optic body 121b as if the shape deformation of the anterior surface is actually higher in the eye lens if a mechanical or fluent force is transferred to the optic portion 121.

Also, a thickness (L1, L2) of the second optic body 121b is desirably thicker in its central region in a mechanical manner. This is also for the purpose that the optic portion has a structure of a natural eye lens, and the central region of the optic portion 221 makes it easier to make shape deformation than the circumferential region, thereby to function more similarly to the natural eye lens.

The haptic portion 223 is coupled to the optic portion 221 from an edge region of the optic portion 221, and the haptic portion 223 has a plurality of shaft bars 222. The shaft bars 222 of the haptic portion 223 may be provided in at least two numbers to transfer a force to the intraocular lens 210 in balance.

At this time, the first support bar 225 is a structural body for coupling at least two ends 222b arranged opposite to the optic portion of the shaft bar, and may become a ring-shaped structural body if the ends 222b arranged opposite to the optic portion are coupled to each other.

Figure 8:
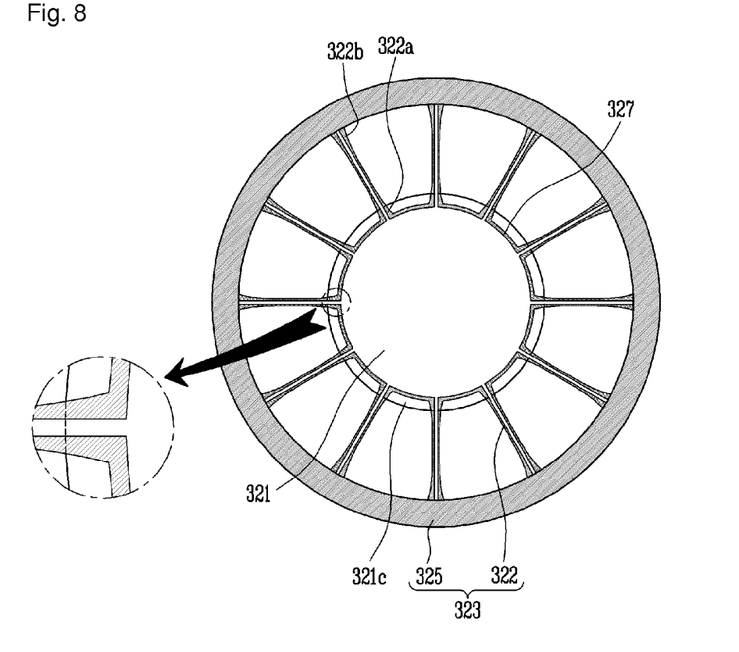

FIG. 8 is a vertical plane view showing an intraocular lens to which the shaft bars in the haptic portion of the intraocular lens are coupled using a first support bar and a second support bar.

The intraocular lens 310 is mainly composed of an optic portion 321 and a haptic portion 323. Here, the optic portion 321 may be configured in the same configuration as in the above-mentioned first embodiment. The haptic portion 323 is coupled to the optic portion 321 from a slight inside edge of the optic portion 321, and includes a first support bar 325, a second support bar 327 and a shaft bar 322.

The shaft bar 322 of the haptic portion 323 may be provided in at least two numbers to transfer a force to the intraocular lens 310 in balance The first support bar 325 is provided to transfer a force, transferred from the intraocular lens supporter (a subsidiary supporter), to the intraocular lens 310 in more balance, as described above in the above embodiments. An outer surface of the first support bar 325 preferably has a round shape as a ring-shaped structure to which the end 322b arranged opposite to the optic portion of the shaft bar 322 is coupled. At this time, the inside of the first support bar 325 may include a flowing space.

Here, the movement of the zonule of Zinn may be more sensitive if the first support bar 325 is further provided, and therefore a control ability by an oil pressure of the intraocular lens 310 is increased, whereas a control ability by an oil pressure of the intraocular lens 310 is decreased but a control ability by a mechanical force is increased if a smaller number of first support bars 325 is provided, as described later.

The second support bar 327 couples ends 322a in the optic portion of the shaft bar 322 to the haptic portion of the intraocular lens 310 to give stability to the shaft bar 322, thereby to transfer a force, transferred through the shaft bar 322, to the optic portion 321 in more balance. At this time, the second support bar 327 may be a structural body that couples the ends 322a in the optic portion of the shaft bar 322, or couples shaft bars s22 around the ends to each other. Also, if a flowing space is formed in the optic portion 321, the flowing space is disposed right in the inside of the optic junction 321c in which only the first optic body 321a and the second optic body 321b are met and pressured to each other, as described later.

If the optic portion 321 and the haptic portion 323 are made of different materials, the end 322a in the optic portion 321 of the shaft bar 322 maximizes its mechanical control ability, and some of the end 622a may be included inside the optic portion 321 for the purpose of the stability of the optic portion 321 in manufacturing the shaft bar 322, as shown in FIG. 8. At this time, in manufacturing the optic portion 321, only the anterior surface and the posterior surface are met and pressured to form an optic junction 321c in a circumferential region regardless of the flowing space.

Then, the optic junction 321c functions to reduce a mechanical or oil pressure deformation in the optic portion 321, but to cause a mechanical or oil pressure deformation more effectively and intensively in the central region of the optic portion 321.

Also, the 322a in the optic portion of the shaft bar 322 may have various shapes, and the control ability by the mechanical force may be different according to the shapes. That is to say, the deformation of the optic portion 321 by the mechanical force is varied with different interaction forces according to the shapes and positions of the above-mentioned materials coupled to the optic portion 321 by means of the end 322a in the optic portion of the shaft bar 322. At this time, the shape deformation of the optic portion 321 is made in a large scale but its stability is low if the interaction force is high, whereas the shape deformation of the optic portion 621 is made in a small scale but its stability is very high if the interaction force is low.

Meanwhile, the end 321a in the optic portion of the shaft bar 322 may be in various shapes such as a convex cone, a convex sphere, circular cylinder, a concave sphere and a concave cone, and the above-mentioned control ability by the mechanical force may be varied according to the shapes. In the case of this embodiment, a circular cylinder is shown in an exploded drawing. Meanwhile, the shaft bar 322 of the haptic portion 323 is made of relatively more rigid materials than the optic portion 321, or the first support bar 325 and the second support bar 327, or has suitable elasticity and restoring force for the mechanical deformation. Also, materials constituting the first face 341 are preferably more flexible than materials constituting the first and second support bars 325, 327. As a result, this is for the purpose of effectively deforming the shape of the optic portion using the force transferred by the movement of the zonule of Zinn induced in the ciliaris muscle. Here, the term flexible means that a material is so soft to deform easily.

Figure 9:
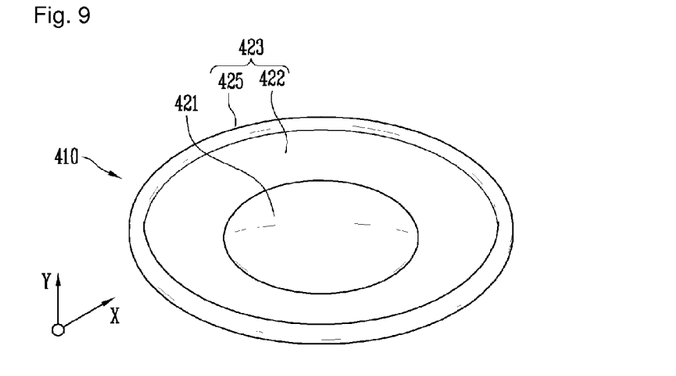

FIG. 9 is a perspective view showing an intraocular lens in which a haptic portion of the intraocular lens is a disk-shaped structural body. In this case, the support bar 425 formed in an end of the connection bar 422 may be a ring-shaped structural body formed in the entire circumference of the disk-shaped structural body, or formed in some section of the circumference.

Figure 10:
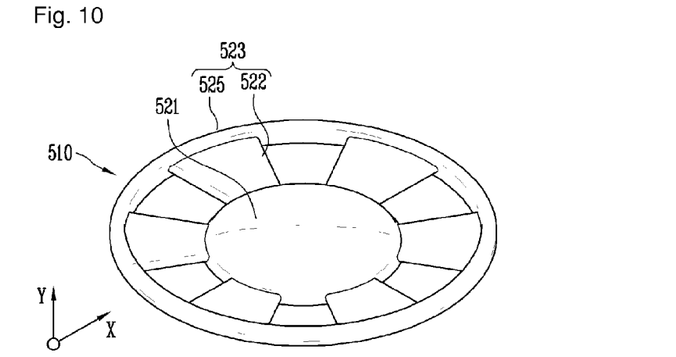

FIG. 10 shows an intraocular lens 510 that are composed of divided disk-shaped structural bodies in which the connection bar 522 is coupled only to one section of the optic portion 521.

Figure 11:
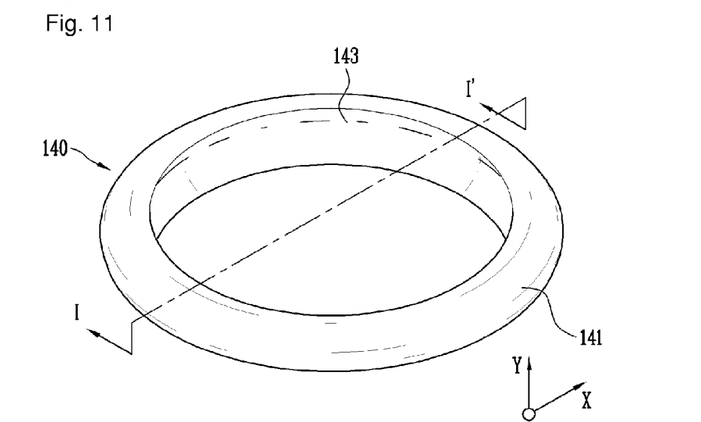
FIG. 11 is a perspective view showing an intraocular lens supporter according to the first embodiment of the present invention.

Meanwhile, FIG. 11 is a perspective view showing one embodiment of an intraocular lens supporter that is suitable for the above-mentioned intraocular lens.

Referring to FIG. 11, the intraocular lens supporter 140 includes a first face 141 and a second face 143. Here, the first face 141 and the second face 143 forms a closed ring-shaped structural body, and a space (not shown) is formed between a membrane constituting the first face 141 and a membrane constituting the second face 143. Materials and thickness of the membranes constituting the first face 141 and the second face 143 are not limited thereto, but a shape deformation ability by movement of the zonule of Zinn will be generally further increased in the intraocular lens supporter if flexible materials or thinner materials are used than if flexible materials or thinner materials are not used.

In order to improve a shape deformation ability according to the movement of the zonule of Zinn, the first face 141 may be composed of flexible materials that are more flexible than the second face 143. Also, if the first face 141 and the second face 143 are composed of the same materials, the first face 141 may be formed at a thinner thickness than the second face 143.

Meanwhile, the entire intraocular lens supporter 110 may be formed integrally in the first face 141 and the second face 143 without any of the empty space between the first face 141 and the second face 143 if the same solid materials as the materials constituting the first face 141 and the second face 143 are formed in the empty space.

The intraocular lens supporter 140 forms a ring-shaped structural body, and the first face 141 forms am outer surface of a ring and the second face 143 forms an inner surface of the ring, and therefore, in the section where the first face 141 is cut along a virtual plane in an equatorial direction (X direction) of the eye lens, the entire extended length is longer than the entire extended length of the second face 143.

Also, a diameter of the intraocular lens supporter 140 is nearly identical to a diameter of the inner surface of the capsular sac. The diameter may be varied according to the humans, but generally ranges from 9 to 13 mm, and a diameter of the equatorial region of the intraocular lens supporter 140 is preferably identical to a diameter of the inner surface of the equatorial region of the patient s eye lens.

A material of the intraocular lens supporter, as used herein, may include silicone, silicone elastomer, silicone polymer, polydimethyl siloxane, polypropylene, polyimide, polybutester, polymethyl methacrylate (PMMA), Microplex PMMA, CQ-UV PMMA, acrylic resin, rigid acrylic, flexible acrylic, acrylic plastic, hydrophobic acrylic, hydrophilic acrylic, hydrophilic acrylic polymer, UV absorbing acrylate, methacrylate copolymer, butyl acrylate, polysiloxane elastomer, UV absorbing polysiloxane, collagen copolymer, gold, hydrogel, 2-hydroxyethyl methacrylate (HEMA), methyl methacrylate (MMA), cellulose acetate butylate (CAB), 2-hydroxy ethyl methacrylate (2-HAMA), n-vinyl pyrrolidone (NVP), polyvinyl pyrrolidone (PVP), methacrylic acid (MA), glycerol methacrylate (GMA), dimethyl siloxane (DMS), polyhydroxyethyl methacrylate (PHEMA), polyethyleneglycol methacrylate (PEGMMA), poly HEMA hydrogel, poly HEMA hydrogel with UV absorption, silicone hydrogel, GMA/HEMA, HEMA/PVP/MA, PVA, HEMA/PVA/MA, HEMA/PVA/MMA, HEMA/MMA, HEMA/NVP, HEMA/NVP/MA, HEMA/NVP/MMA, HEMA/Acryl, and HEMA/PC.

Figure 12:
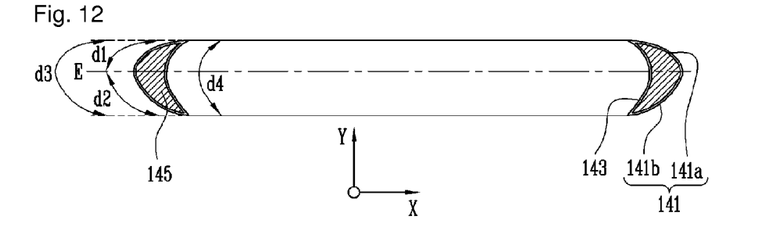
FIG. 12 is a cross-sectional view taken from a line I-I' as shown in FIG. 11.

FIG. 12 is a cross-sectional view taken from a line I-I' as shown in FIG. 11. Referring to FIG. 12, the first face 141 is a surface which is in contact with an inner surface of the capsular sac in at least one point, and the first face 141 is a section corresponding respectively to an anterior capsule and a posterior capsule of the capsular sac, and has an anterior portion 141a and a posterior portion 141b divided by an equator (E).

In a section cut along a virtual plane in a visual axis direction (Y direction) of the eye lens visual axis direction, the anterior portion 141a of the first face 141 has a larger curvature than the posterior portion 141b. This is why the section where the first face 141 is cut along a virtual plane in a visual axis direction (Y direction) of the eye lens is formed in the same shape as a sectional shape of an equatorial region of a natural eye lens. As described above, the anterior surface in the central region of the eye lens has a smaller curvature than the posterior surface, but the anterior surface and the posterior surface have a reverse shape as it approaches an equatorial region.

More particularly, the first face 141 is formed in the same sectional shape as the inherent eye lens of a patient that undergoes a surgical operation. A photograph of a sectional shape of the patient eye lens before the surgical operation may be taken using ultrasonic imaging, CT, and MRI. The first face 141 has a sectional shape between mydriasis and miosis, but may have a shape that accord with the sectional shape of the eye lens having a pupil size of 3 to 4 mm.

Accordingly, the first face 141 accords with a shape of the inner surface in the equatorial region of the capsular sac.

In the section cut along a virtual plane in a visual axis direction (Y direction) of the eye lens, the first face 141 is preferably provided in at least a length as much as ¾ to 3 times of a length (d5, see FIG. 19) of a region where a zonule of Zinn is coupled to an outer surface of the capsular sac. A force transferred to the intraocular lens with the movement of the zonule of Zinn is not effectively transferred if the first face 141 is formed in a smaller length range than ¾ times, and the optic portion of the intraocular lens may be covered if the first face 141 is formed in a greater length range than 3 times.

More preferably, an extended length (d1) from the equator (E) to an end point of the anterior portion 141a, and an extended length (d2) from the equator (E) to an end point of the posterior portion 141b may generally range from 1 to 4.2 mm in the section cut along a virtual plane in a visual axis direction (Y direction) of the eye lens. It is difficult to insert the intraocular lens supporter in the surgical operation and the optic portion is too small if the extended length exceeds 4.2 mm, whereas the intraocular lens supporter is provided in an inner position than a point where the second zonule portion of the zonule of Zinn is coupled to the capsular sac if the extended length is less than 1 mm, and therefore a force transferred by the movement of the zonule of Zinn induced in the ciliaris muscle is not suitably transferred to the intraocular lens, which leads to insufficient volume change in the intraocular lens supporter. At this time, in the section where the first face 141 is cut along a virtual plane in a visual axis direction (Y direction) of the eye lens, the total length may range from 2 to 8 mm.

At this time, the extended length (d1) from the equator (E) to the end point of the anterior portion 141a may be identical to, or different from the extended length (d2) from the equator (E) to the end point of the posterior portion 141b, but the length of d2 will be generally longer than the length of d1.

Meanwhile, a roughness of the first face 141 may be higher or a adhesive may be added to facilitate mounting of the intraocular lens supporter in the capsular sac. Therefore, the intraocular lens supporter may be fixed in a stable position. A tissue glue or glue may be, for example, used as the adhesive.

The second face 143 is a surface to which the intraocular lens is coupled, and the total extended length (d4) in the section where the second face 143 is cut along a virtual plane in a visual axis direction (Y direction) of the eye lens is shorter than, or identical to the total extended length (d3=d1+d2) of the first face. A fact that the total extended length (d4) in the section where the second face 143 is cut along a virtual plane in a visual axis direction (Y direction) of the eye lens is smaller than or identical to the total extended length (d3=d1+d2) of the first face 141 is for the purpose of amplifying or maintaining a force transferred to the first face 141 when the force is transferred to the second face 143 in the zonule of Zinn.

That is to say, the movement and volume changes are more induced according to the movement of the first face 141 since the first face 141 has a shorter extended length than the second face 143. When a force F1 is transferred to the zonule of Zinn in the first face 141, a force transferred to the second face 143 becomes F2 (=kF1, k≥1). At this time, k is a constant determined by a length ratio of d3 and d4. The length ratio of d3 and d4 may be varied according to the ability of the zonule of Zinn in patients, and a length of d4 is preferably generally longer as much as 0.4 to 1 times than a length of d3.

An inner space between the first face 141 and the second face 143 is filled with gases, liquids or solids. The inner space may be filled with the gases, such as air or inert gases, namely, nitrogen, argon, neon, helium, etc., and filled with the liquids, such as water or silicone, sodium hyaluronate, chondroitin sulfate, hydroxypropyl methylcellulose, polyacrylamide, etc.

A shape deformation ability of the intraocular lens supporter is more enhanced by the movement of the zonule of Zinn of the intraocular lens supporter if materials having a high fluidity are used as the materials filled in the space 145 between the first face 141 and the second face 143 than if materials having a high fluidity are not used.

Various modifications of the intraocular lens supporter may be made in the present invention. That is to say, the intraocular lens supporters as shown in FIG. 13, FIG. 14, FIG. 15 and FIG. 16 may be used.

Figure 13:
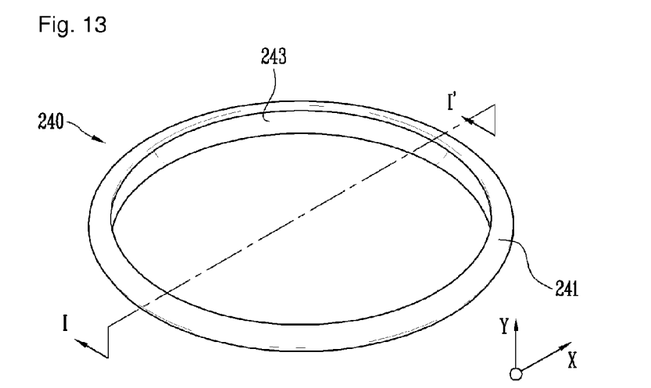
FIG. 13 to FIG. 16 are diagrams showing various modified examples of an intraocular lens supporter used in the present invention.
Figure 14:
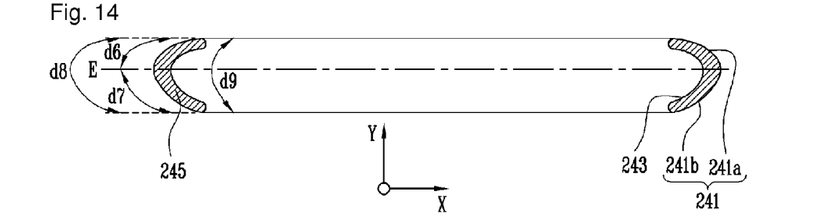

FIG. 13 shows an intraocular lens supporter having no space formed inside the intraocular lens supporter, and FIG. 14 is a cross-sectional view taken from a line I-I' as shown in FIG. 13. In this case, the intraocular lens supporter 240 induces a shape deformation of the intraocular lens through the movement of the zonule of Zinn using only the mechanical deformation.

Figure 15:
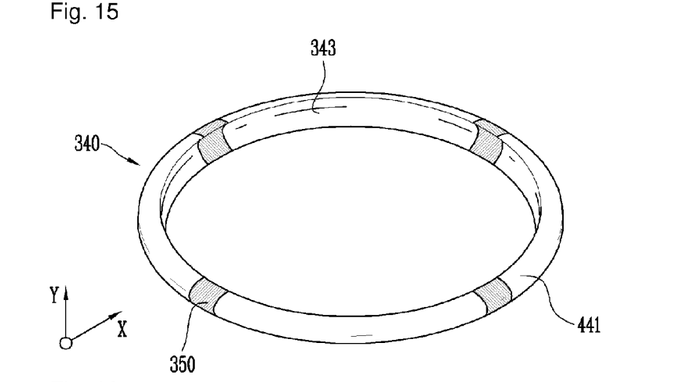

The intraocular lens supporter 340 in the eyeball as shown in FIG. 15 is a closed ring-shaped structural body, and has a flexible connection unit 350 with at least one section having a higher flexibility then other sections.

The flexible connection unit 350 is a cut region having a smaller area than the capsular sac, and aids to insert the intraocular lens supporter 340 into the capsular sac. That is to say, if the intraocular lens supporter 340 is inserted into the capsular sac, the flexible connection unit 350 is bended, and therefore the intraocular lens supporter 310 may be inserted into the capsular sac although it has a small cut region.

Figure 16:
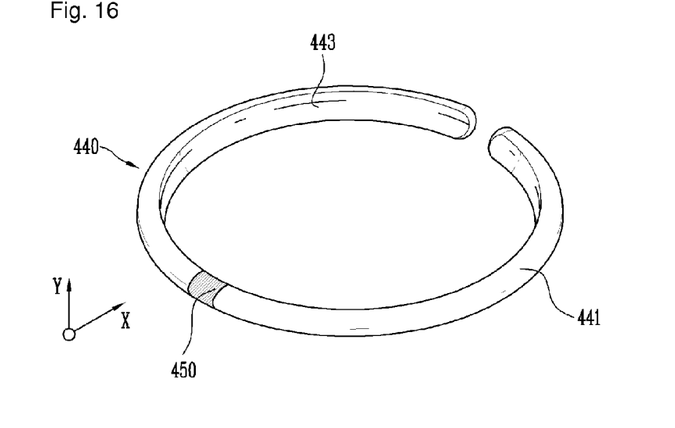

As shown in FIG. 16, the intraocular lens supporter 440 has an open ring-shaped structure other than the closed ring-shaped structure, and also has at least one flexible connection unit 450. As a result, the intraocular lens may be inserted into the capsular sac while the cut region is reduced to a smaller.

Figure 17:
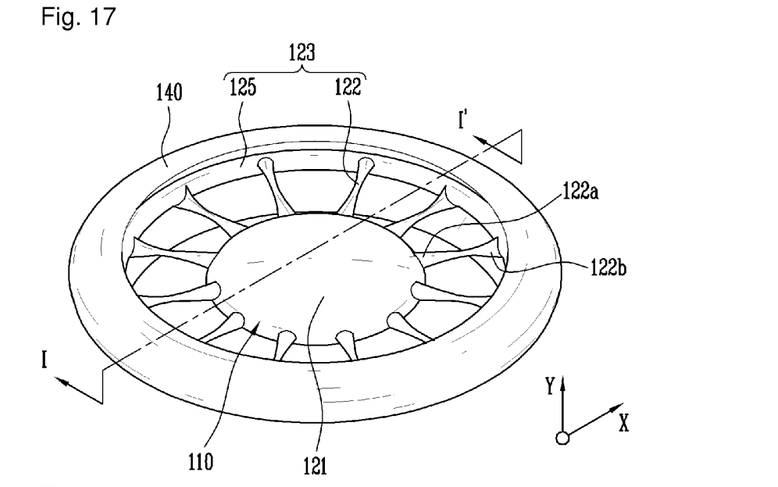
FIG. 17 is a perspective view showing an intraocular lens assembly in which the intraocular lens according to the first aspect is coupled to the intraocular lens supporter according to the first embodiment of the present invention.
Figure 18:
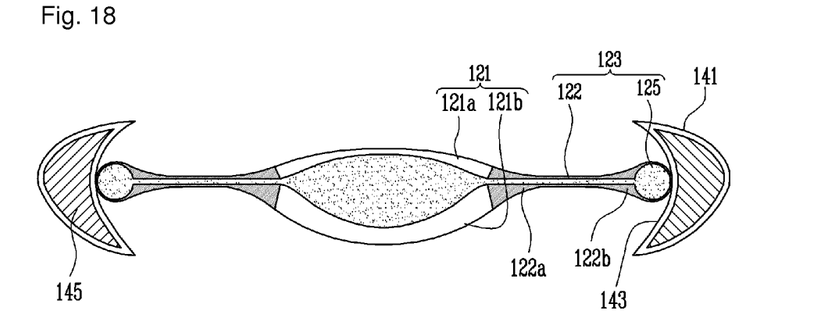
FIG. 18 is a cross-sectional view taken from a line I-I' as shown in FIG. 17.

FIG. 17 is a perspective view showing that the intraocular lens is coupled to the intraocular lens supporter according to the present invention, and FIG. 18 is a cross-sectional view taken from a line I-I' as shown in FIG. 17.

Referring to FIGS. 17 and 18, the intraocular lens 110 is supported by the intraocular lens supporter 140, and the second face 143 of the intraocular lens supporter 140, and the support bar 125 of the haptic portion 123 of the intraocular lens 110 inserted inwardly into the capsular sac are disposed inside of a ring shape of the intraocular lens supporter 140 while the second face 143 and the support bar 125 are in contact with each other.

Hereinafter, an interaction of the intraocular lens assembly according to the first embodiment of the present invention will be described in detail with reference to the accompanying drawings.

Figure 19:
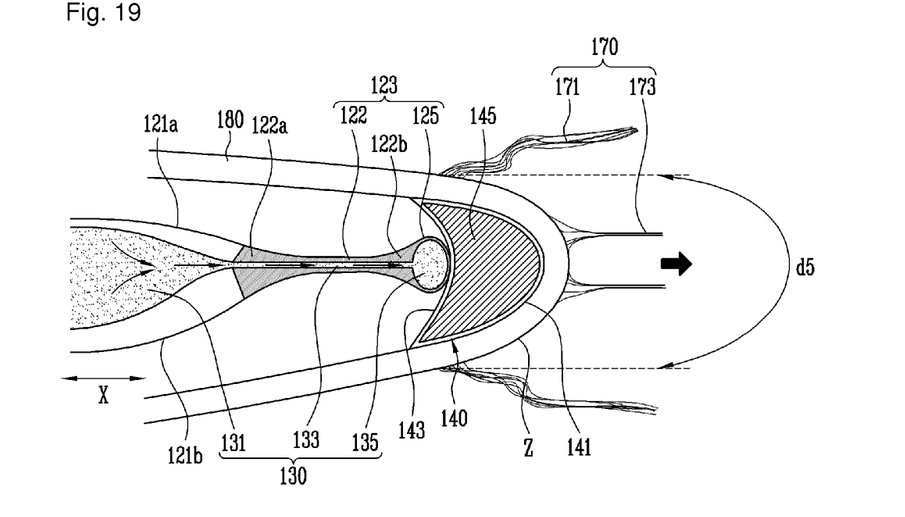
FIG. 19 and FIG. 20 are illustrative views showing interactions of a zonule of Zinn, an intraocular lens, an intraocular lens supporter and a capsular sac when focused on respectively a long distance and a short distance according to the first embodiment of the present invention.
Figure 20:
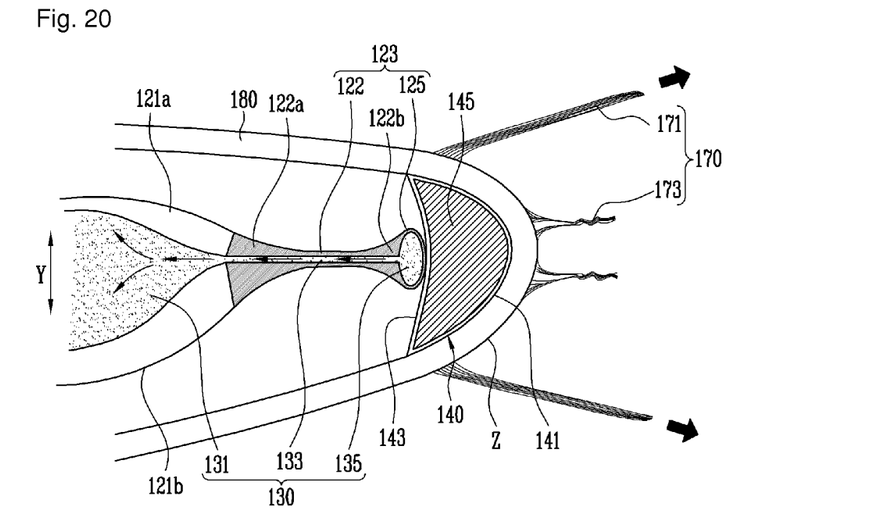

FIG. 19 and FIG. 20 are illustrative views showing interactions of a zonule of Zinn, an intraocular lens, an intraocular lens supporter and a capsular sac when focused on respectively a long distance and a short distance object according to the first embodiment of the present invention.

The zonule of Zinn 170 is coupled to the outer surface of the capsular sac 180, and the zonule of Zinn 170 is coupled to a region around the equator of the capsular sac 180, and therefore a region to which the zonule of Zinn is coupled is referred to as a connection region for zonule of Zinn (Z) in this application.

When focused on a long distance object, a first zonule portion 173 coupled to the center of the connection region for zonule of Zinn (Z) in the capsular sac 180 is pulled taut, and a second zonule portion 171 coupled to a circumference of the equatorial region of the connection region for zonule of Zinn in the capsular sac 180 is relaxed.

At this time, the equatorial region of the capsular sac 180 is extended in a radial direction (X) of the eye lens, and the shape of the first face 141 of the intraocular lens supporter 140 that is in contact with the capsular sac is also extended in a radial direction of the eye lens. Then, the second face 143 of the intraocular lens supporter 140 is also deformed to correspond to the shape deformation of the first face 141, and the support bar 125 of the haptic portion 122 that is in contact with the second face 143 is also extended in the radial direction. Accordingly, the intraocular lens 110 coupled to the support bar 125, in particularly the flexible optic portion 121, is also extended in the same direction to make the optic portion 121 more convex.

In addition, the fluid filled in the flowing space 130 of the intraocular lens 110 is also subject to external forces, and the intraocular lens 110 is extended in a radial direction of the eye lens when focused on a long distance object, and therefore the fluid in the flowing space 130 is distributed at a higher amount in the third space portion 135 than the first space portion 131 and the second space portion 133. Therefore, the shapes of the optic portions 121; 121a, 121b of the intraocular lens 110 are deformed more effectively to make the optic portion 121 less convex.

When focused on a short distance object, the first zonule portion 173 coupled to the central region of the connection region for zonule of Zinn (Z) in the capsular sac 180 is relaxed, and the second zonule portion 171 coupled to a circumference of the connection region for zonule of Zinn (Z) in the capsular sac 180 is pulled taut.

Accordingly, the equatorial region of the capsular sac 180 is protruded in a visual axis direction (Y direction) of the eye lens, and therefore the intraocular lens 110 with elasticity arranged inside the capsular sac 180 is also extended in the same direction (Y direction) to be deformed into a suitable shape to see at a short distance.

At the same time, the fluid filled in the flowing space of the intraocular lens 110 is also subject to the external forces. At this time, the fluid in the third space portion 135 is gathered in the first space portion 131 through the second space portion 133 since the external forces are applied to a flexible region of the support bar of the intraocular lens 110 when focused on a short distance object, and therefore the shape of the optic portion 121 of the intraocular lens 110 is deformed more effectively to make the optic portion 121 more convex.

Also, if the fluid is gathered in the first space portion 131 of the optic portion 121, the first optic body 121a is formed in a smaller thickness than the second optic body 121b, and therefore the optic portion 121 is made more convex toward the anterior surface. As a result, the intraocular lens may be deformed similarly to an actual eye structure. Accordingly, the intraocular lens assembly according to this embodiment may effectively control a shape of the intraocular lens even if an ability of the ciliaris muscle is lowered since a force transferred from the zonule of Zinn is mechanically transferred to the intraocular lens 310, and also transferred to the intraocular lens 110 by means of the oil pressure to effectively control a thickness of the optic portion 121 of the intraocular lens 110.

As described above, the use of the intraocular lens assembly according to this embodiment makes it possible to control a thickness of the intraocular lens 110 like the natural eye lens. That is to say, the use of the intraocular lens assembly according to this embodiment may make it possible to control a thickness of the intraocular lens as if a thickness of the natural eye lens is controlled by the interaction of the capsular sac 180 coupled to the zonule of Zinn.

In particular, an interaction force by a mechanical force complementarily acts together with an interaction force by an oil pressure in this embodiment. The use of more flexible materials, thinner materials or fluids as more flexible media makes the deformation of the optic portion 121 by the oil pressure more increased, and the use of less flexible materials, thicker materials or fluids as more compact media makes the deformation of the optic portion 121 by the mechanical force more increased.

The deformation of the optic portion 121 by the mechanical force is varied with different interaction forces according to the shapes and positions of the above-mentioned materials inserted into the optic portion 121 by the end 122a in the optic portion of the shaft bar. At this time, the shape deformation of the optic portion 121 is made in a large scale but its stability is low if the interaction force is high, whereas the shape deformation of the optic portion 121 is made in a small scale but its stability is very high if the interaction force is low.

The suitable materials and fluids may be selected to adjust a control ability of the intraocular lens since the deformation of the optic portion 121 is made in a higher level by the oil pressured other than the mechanical force.

An intraocular lens with very high control ability has a disadvantage that it has a short lift span due to the repeated excessive deformation and the thin materials of the optic portion, but it is suitable for old patients who has a poor control ability of the eye.

Figure 21:
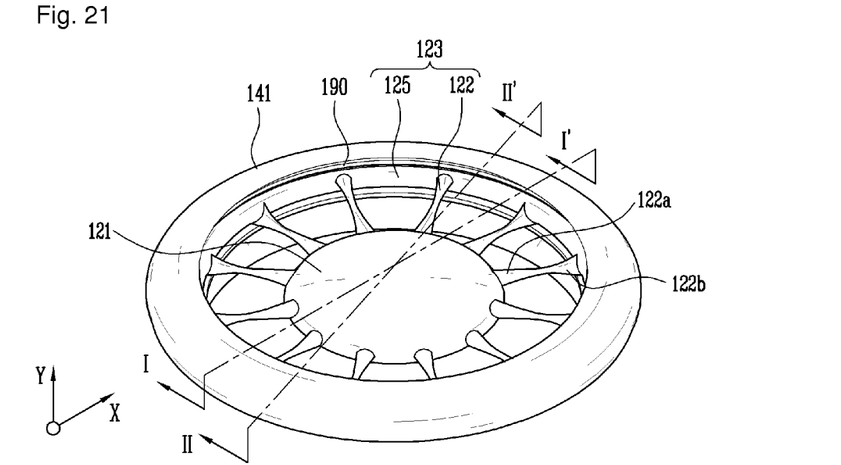
FIG. 21 is a perspective view showing an intraocular lens assembly according to the second embodiment of the present invention.
Figure 22:
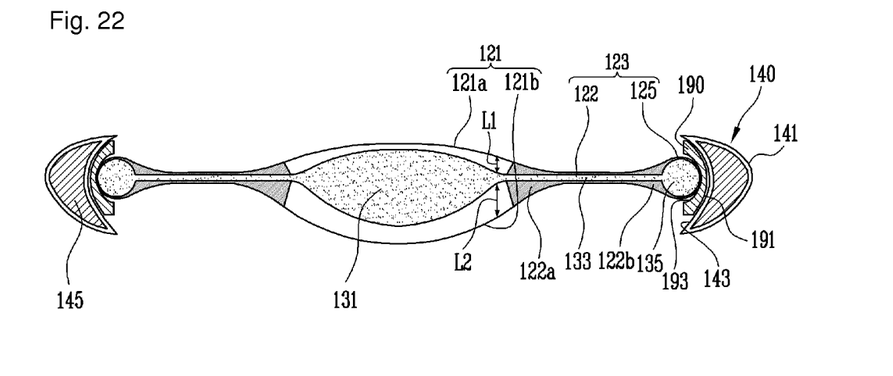
FIG. 22 is a cross-sectional view taken from a line I-I' as shown in FIG. 21.
Figure 23:
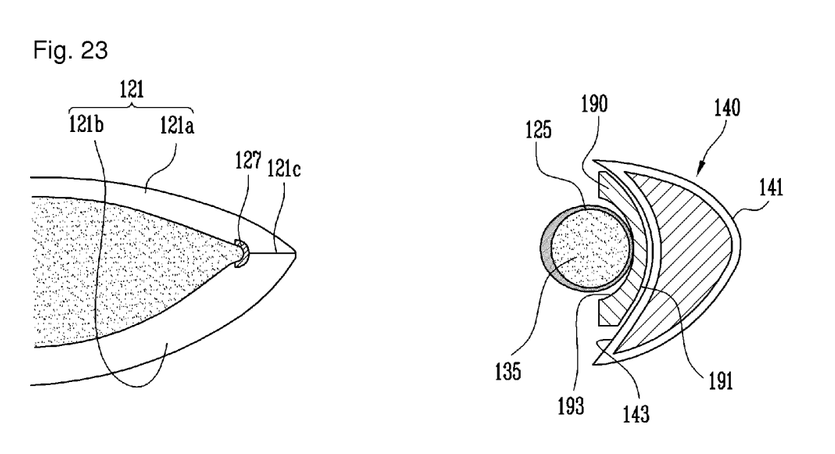
FIG. 23 is a cross-sectional view taken from a line II-II' as shown in FIG. 21.

Also, an intraocular lens with moderate control ability has an advantage that it has a long lift span, and therefore the intraocular lens is suitable for high myopic correction for young people. FIG. 21 is a perspective view showing an intraocular lens assembly according to the second embodiment of the present invention, FIG. 22 is a cross-sectional view taken from a line I-I' as shown in FIG. 21, and FIG. 23 is a cross-sectional view taken from a line II-II' as shown in FIG. 21. The same parts as the first embodiment has the same reference numerals in this embodiment.

Referring to FIGS. 21, 22 and 23, the intraocular lens assembly according to this embodiment further includes a separate subsidiary supporter 190 between the intraocular lens 110 and the intraocular lens supporter 140. The subsidiary supporter 190 includes a first face 111 with a shape facing the second face 113 of the intraocular lens supporter 140; and a second face 113 with a shape facing the outer surface of the first support bar 125 in the haptic portion 121 of the intraocular lens 110.

The subsidiary supporter 190 may buffer a force transferred from the capsular sac 180 to the intraocular lens 110, and easily fix the intraocular lens 110 in the intraocular lens supporter 140 at the same time.

The same materials as the materials of the above-mentioned intraocular lens 110 and intraocular lens supporter 140 may be used for the subsidiary supporter 190.

Hereinafter, one case of using an intraocular lens having a second support bar formed therein will be described in detail in this embodiment, as shown in FIG. 8.

In particular, a surface facing the optic portion of the first support bar 125 includes a section having a larger thickness than a surface facing the intraocular lens supporter 140, as shown in FIG. 23. At this time, the surface facing the optic portion 121 of the first support bar 125 may be made of flexible materials that are less flexible than the surface facing the intraocular lens supporter 140. This for the purpose of functioning as a wheel capable of making the surface facing the optic portion 121 less flexible, thereby to strongly fix the shaft bar in the support bar.

Also, a surface where the second support bar 127 is in contact with the optic portion 121 is formed with a shape corresponding to an equatorial surface of the optic portion 121, namely a shape that is concave toward the center of the optic portion 121. As a result, a force transferred from the zonule of Zinn may be transferred to the optic portion 121 more effectively.

The intraocular lenses according to the above-mentioned embodiments of the present invention may be formed into one piece as described above, or formed with several pieces. For example, if the intraocular lens is formed into one piece, it may be manufactured using various plastic forming methods, and if the intraocular lens is formed with several pieces, it may also be easily manufactured through the attachment of the pieces using an adhesive, a heat, a laser, etc.

The description proposed herein is just a preferable example for the purpose of illustrations only, not intended to limit the scope of the invention, so it should be understood that other equivalents and modifications could be made thereto without departing from the spirit and scope of the invention as apparent to those skilled in the art. Therefore, it should be understood that the present invention might be not defined within the scope of which is described in detailed description but within the scope of which is defined in the claims and their equivalents.

The invention claimed is:

1. An intraocular lens assembly adapted to be inserted inwardly into a capsular sac, comprising:
    an intraocular lens an optic portion and a haptic portion; and
    an intraocular lens supporter wherein the intraocular lens supporter is a structural ring body configured so that a force is transferred to the intraocular lens due to movement of a zonule of Zinn, comprising:
    a first face configured to come in contact with an inner surface of the capsular sac in at least one point when inserted into the capsular sac, and
    a second face arranged opposite to the first face,
    wherein, the intraocular lens supporter comes in contact with the haptic portion of the intraocular lens and is extended along an equatorial region of the capsular sac when inserted into the capsular sac and in a section where the structural body is cut along a virtual plane in a visual axis direction of an eye lens, the first face is provided at a length as much as ¾ to 3 times of a length of a region where a zonule of Zinn is coupled to an outer surface of the capsular sac,
    the first face has a first extended length from one end portion to another end portion in the section where the structural body of the first face is cut along the virtual plane in the visual axis direction of the eye lens of 2 to 8 mm,
    the second face has a second extended length from one end portion to another end portion on the section where the second face is cut along the virtual plane in the visual axis direction of the eye lens, and
    wherein the second extended length of the second face is longer by 0.4 to 1 times that of the first extended length of the first face, and
    the first face has an anterior portion and a posterior portion corresponding respectively to an anterior capsule and a posterior capsule when inserted into the capsular sac divided by an equator of the capsular sac, wherein the equator is a vertical direction relative to the visual axis direction of the eye lens.

2. The intraocular lens assembly according to claim 1, wherein the optic portion includes a first optic body whose central region has a smaller thickness than a circumference of the central region and a second optic body a second optic body coupled to the first optic body and whose central region has a same or greater thickness as/than the center region of the first optic body, the first optic body made of materials that are more flexible than a second optic body.

3. The intraocular lens assembly according to claim 2, wherein the first optic body includes an inner surface and an outer surface, the inner surface and the outer surface is a spherical surface or an aspheric surface, and the inner surface is a spherical surface having a greater curvature than the outer surface, or a more aspheric surface.

4. The intraocular lens assembly according to claim 1, wherein the haptic portion includes a connection bar coupled to the optic portion and first support bar coupled to a circumference of the connection bar, the first support bar configured to come in contact with an inner surface of the capsular sac, the first support bar having a surface that is configured to come in contact with an inner surface of the capsular sac and has a round shape.

5. The intraocular lens assembly according to claim 4, wherein the connection bar is a shaft bar-shaped structural body coupled to at least two sections in a circumference of the optic portion.

6. The intraocular lens assembly according to claim 5, wherein the first support bar couples at least two ends of the shaft bars of the connection bar.

7. The intraocular lens assembly according to claim 5, wherein the first support bar is a ring-shaped structural body for coupling all ends of the shaft bars of the connection bar.

8. The intraocular lens assembly according to claim 5, wherein the first support bar of the haptic portion is made of flexible materials that are more flexible than the shaft bar, and the optic portion is made of flexible materials that are more flexible than the first support bar.

9. The intraocular lens assembly according to claim 5, wherein both ends of the shaft bar have a larger cross-sectional area than a central region of the shaft bar.

10. The intraocular lens assembly according to claim 5, wherein the both ends of the optic portion of the shaft bar further include a ring-shaped second support bar for coupling ends of the optic portion.

11. The intraocular lens assembly according to claim 10, wherein an inner surface of the second support bar has a concave shape toward the central region of the optic portion.

12. The intraocular lens assembly according to claim 10, wherein the second support bar is formed in a circumference of the optic portion.

13. The intraocular lens assembly according to claim 10, wherein the second support bar is includes inside the optic portion.

14. The intraocular lens assembly according to claim 4, wherein the connection bar is a disk-shaped structural body coupled to the entire section of the circumference of the optic portion.

15. The intraocular lens assembly according to claim 4, wherein the connection bar is a disk-shaped structural body coupled to at least two sections of the circumference of the optic portion and divided into at least two sections.

16. The intraocular lens assembly according to claims 14 or 15, wherein the first support bar is formed around an end of the disk-shaped connection bar.

17. The intraocular lens assembly according to claim 4, wherein the optic portion and the first support bar are made of flexible materials that are more flexible than the connection bar.

18. The intraocular lens assembly according to claim 4, wherein the optic portion and the first support bar are made of the same flexible materials as the connection bar, and formed with a thickness thinner than that of the connection bar.

19. The intraocular lens assembly according to claim 4, wherein the first support bar is a structural body that is extended along an end of the connection bar, and a surface of the first support bar that is in contact with an inner surface of the intraocular lens supporter accords with a shape of the inner surface of the intraocular lens supporter.

20. The intraocular lens assembly according to claim 4, wherein a surface facing the optic portion of the first support bar includes a section that is formed at a thickness greater than a surface facing the intraocular lens supporter.

21. The intraocular lens assembly according to claim 4, wherein a surface facing the optic portion of the first support bar includes a section that is formed of flexible materials that are less flexible than a surface facing the intraocular lens supporter.

22. The intraocular lens assembly according to claim 1, wherein a flowing space is further provided inside the intraocular lens.

23. The intraocular lens assembly according to claim 22, wherein the flowing space is provided at least between a first optic body and a second optic body of the optic portion.

24. The intraocular lens assembly according to claim 23, wherein the second optic body has a thinner thickness in its central region than its circumference.

25. The intraocular lens assembly according to claim 23, wherein the second optic body includes an inner surface and an outer surface, and the inner surface and the outer surface are a spherical surface or an aspheric surface, and the inner surface has a larger curvature than the outer surface.

26. The intraocular lens assembly according to claim 24, wherein the first optic body includes a section that where grows thicker as its central region approaches its circumference.

27. The intraocular lens assembly according to claim 22, wherein the flowing space includes a first space portion provided between a first optic body and a second optic body of the optic portion; a second space portion provided inside the connection bar; and a third space portion provided inside the first support bar.

28. The intraocular lens assembly according to claim 27, wherein the first space portion, the second space portion and the third space portion are coupled to each other.

29. The intraocular lens assembly according to claim 27, wherein a shape of the first space portion is formed in a convex lens shape having at least one convex surface.

30. The intraocular lens assembly according to claim 29, wherein a subsidiary supporter is further provided between the intraocular lens and the intraocular lens supporter, the subsidiary supporter including a first face with a shape facing the second face of the intraocular lens supporter; and a second face with a shape facing the outer surface of the haptic portion of the intraocular lens.

31. The intraocular lens assembly according to claim 27, wherein a shape of the first space portion is formed in an aspheric convex lens shape having at least one aspheric surface.

32. The intraocular lens assembly according to claim 27, wherein the first optic body and the second optic body have the same thickness, and include sections that have an increasing thickness as their central regions approach their circumference, respectively.

33. The intraocular lens assembly according to claim 22, wherein the flowing space is filled with one selected from the group consisting of liquid, gas, and fluent solid.

34. The intraocular lens assembly according to claim 33, wherein the liquid is one selected from the group consisting of water, silicone, sodium hyaluronate, chondroitin sulfate, hydroxypropyl methylcellulose and polyacrylamide.

35. The intraocular lens assembly according to claim 33, wherein the gas is one selected from the group consisting of air, nitrogen, helium, neon and argon.

36. The intraocular lens assembly according to claim 1, wherein materials of the intraocular lens and the intraocular lens supporter are composed of one selected from the group consisting of silicone, silicone elastomer, silicone polymer, polydimethyl siloxane, polypropylene, polyimide, polybutester, polymethyl methacrylate (PMMA), Microplex PMMA, CQ-UV PMMA, acrylic resin, rigid acrylic, flexible acrylic, acrylic plastic, hydrophobic acrylic, hydrophilic acrylic, hydrophilic acrylic polymer, UV absorbing acrylate, methacrylate copolymer, butyl acrylate, polysiloxane elastomer, UV absorbing polysiloxane, collagen copolymer, gold, hydrogel, 2-hydroxyethyl methacrylate (HEMA), methyl methacrylate (MMA), cellulose acetate butylate (CAB), 2-hydroxy ethyl methacrylate (2-HAMA), n-vinyl pyrrolidone (NVP), polyvinyl pyrrolidone (PVP), methacrylic acid (MA), glycerol methacrylate (GMA), dimethyl siloxane (DMS), polyhydroxyethyl methacrylate (PHEMA), polyethyleneglycol methacrylate (PEGMMA), poly HEMA hydrogel, poly HEMA hydrogel with UV absorption, silicone hydrogel, GMA/HEMA, HEMA/PVP/MA, PVA, HEMA/PVA/MA, HEMA/PVA/MMA, HEMA/MMA, HEMA/NVP, HEMA/NVP/MA, HEMA/NVP/MMA, HEMA/Acryl, and HEMA/PC.

* * * * *